(12) United States Patent
Sakai

(10) Patent No.: US 7,038,775 B2
(45) Date of Patent: May 2, 2006

(54) SPECTROSCOPIC DEVICE

(75) Inventor: Shirou Sakai, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 0 days.

(21) Appl. No.: 10/482,779

(22) PCT Filed: Jul. 5, 2002

(86) PCT No.: PCT/JP02/06864

§ 371 (c)(1),
(2), (4) Date: Jul. 26, 2004

(87) PCT Pub. No.: WO03/004982

PCT Pub. Date: Jan. 16, 2003

(65) Prior Publication Data

US 2004/0239930 A1    Dec. 2, 2004

(30) Foreign Application Priority Data

Jul. 5, 2001    (JP) .............................. 2001-205307

(51) Int. Cl.
*G01B 11/00*    (2006.01)

(52) U.S. Cl. .................................................... 356/328

(58) Field of Classification Search ................ 356/328, 356/300–334

See application file for complete search history.

(56) References Cited

U.S. PATENT DOCUMENTS 4,540,282 A * 9/1985 Landa et al. ................ 356/328
5,481,158 A * 1/1996 Kato et al. .................. 313/533
2003/0048442 A1* 3/2003 Xiao .......................... 356/328

FOREIGN PATENT DOCUMENTS

| EP | 0 597 667 A1 | 5/1994 |
|----|--------------|--------|
| JP | 58-045524 | 3/1983 |
| JP | 61-12238 | 7/1986 |
| JP | 05-180761 | 7/1993 |
| JP | 07-103823 | 4/1995 |
| JP | 2000-009533 | 1/2000 |
| JP | 2001-108614 | 4/2001 |

* cited by examiner

*Primary Examiner*—Gregory J Toatley, Jr.
*Assistant Examiner*—Isiaka O. Akanbi
(74) *Attorney, Agent, or Firm*—Drinker Biddle & Reath LLP

(57) ABSTRACT

A spectroscopic system according to the present invention 10 comprises: an optical fiber bundle 12 whose emitting end 12a is arranged in a vertical direction; a slit 16 which is arranged so as to oppose the emitting end 12a of the optical fiber bundle 12; spectroscopic element arrangement means 20 which can switchably arrange either a first diffraction grating 23 in which grooves extending along the vertical direction are arranged in a horizontal direction at a predetermined groove density, or a second diffraction grating 24 in which grooves extending along the vertical direction are arranged in the horizontal direction at a groove density larger than that of the first diffraction grating 23, on an optical path of light which is emitted from the emitting end 12a of the optical fiber bundle 12 and passes through the slit 16; and a photomultiplier tube 30 in which a plurality of anodes 53 extending along the vertical direction are arranged in the horizontal direction.

6 Claims, 13 Drawing Sheets

SPECTROSCOPIC DEVICE

TECHNICAL FIELD

The present invention relates to a spectroscopic system, and more particularly to a spectroscopic system which can spectroscopically detect weak light with high sensitivity.

BACKGROUND ART

An emission spectral analysis method and a fluorescence spectral analysis method have been established as an analysis method of a trace constituent. In these spectrum analyses, it is required to spectroscopically detect weak light emission or fluorescence which is emitted from a sample. Thus, as a system for spectroscopically detecting the weak light emission or the fluorescence, a spectroscopic system comprising a spectroscopic element and a photomultiplier tube has been developed.

DISCLOSURE OF THE INVENTION

As a result of examining a prior art technique described above, the inventor has discovered the following problems. That is, in order to improve accuracy of an emission spectral analysis or a fluorescence spectral analysis, it is required to spectroscopically detect weak light emission and fluorescence with higher sensitivity as much as possible, and for that purpose, it is required to further improve the sensitivity of a spectroscopic system. In addition, since the prior art spectroscopic system described above primarily has a low wavelength resolution, it is also required to improve a wavelength resolution.

The present invention has been made to solve the problems described above, and the object thereof is to provide a spectroscopic system which can spectroscopically detect weak light with higher sensitivity and high wavelength resolution.

The spectroscopic system according to the present invention comprises: an optical fiber bundle whose emitting end is arranged in a first direction; a slit which is arranged so as to oppose the emitting end of the optical fiber bundle; spectroscopic element arrangement means which can switchably arrange either a first diffraction grating in which grooves extending along a second direction are arranged at a predetermined groove density in a direction to intersect the second direction, or a second diffraction grating in which grooves extending along the second direction are arranged at a groove density larger than that of the first diffraction grating in a direction to intersect the second direction, on an optical path of light which is emitted from the emitting end of the optical fiber bundle and passes through the slit; and a photomultiplier tube in which a plurality of anodes extending along a third direction are arranged in a direction to intersect the third direction. The first direction, the second direction, and the third direction are substantially the same direction.

This spectroscopic system comprises a two-dimensional photomultiplier tube, which arranges a plurality of anodes extending in the third direction, as a detector. The plurality of these anodes are arranged in a direction to intersect the third direction. Here, the first direction which is an arrangement direction of the emitting end of the optical fiber bundle, the second direction which is a formation direction of the groove of the first and the second diffraction gratings, and the third direction in which the anodes extend are substantially the same direction. Therefore, this makes it possible to detect light, which is emitted from the emitting end of the optical fiber bundle to pass through the slit, and entered into the diffraction grating to be demultiplexed into individual wavelengths light, by each of the plurality of anodes by sufficiently utilizing an effective area of the photomultiplier tube. Thus, by sufficiently utilizing the effective area of the photomultiplier tube, this makes it possible to spectroscopically detect weak light with higher sensitivity. In addition, since the spectroscopic element arrangement means can switchably arrange the first diffraction grating which has the predetermined groove density, and the second diffraction grating which has the groove density larger than that of the first diffraction grating, it becomes possible not only to spectroscopically detect light with a wider wavelength range by the first diffraction grating, but also to increase the wavelength resolution by spectroscopically detecting the light with a narrow wavelength range by the second diffraction grating.

The spectroscopic system according to the present invention may be characterized by comprising optical path length adjustment means of adjusting an optical path of the light from the emitting end of the optical fiber bundle to the photomultiplier tube. Thus, this makes it possible to form a tight-focused image on the photomultiplier tube.

The optical path length adjustment means may be characterized by having a guide tube for guiding the emitting end of the optical fiber bundle in a predetermined direction. Thus, the emitting end of the optical fiber bundle is guided by the guide tube, and the optical path length is adjusted.

The spectroscopic system according to the present invention may be characterized by comprising a filter, which is removably arranged on an optical path, for cutting higher order light. Thus, this makes it possible to suppress the effect of the higher order light at the time of measurement in a long wavelength band.

The spectroscopic system according to the present invention may be characterized by comprising a first lens for guiding the light to the first diffraction grating or the second diffraction grating, and a cylindrical lens arranged in front of the first lens. Thus, this makes it possible to reliably guide the light to the first diffraction grating or the second diffraction grating by the first lens, and also to remove a chromatic aberration or a spherical aberration due to the first lens by the cylindrical lens.

In the spectroscopic system according to the present invention, the spectroscopic element arrangement means may be characterized by comprising a back board which mounts the first and the second diffraction gratings and extends along the second direction, and a rotary dial for rotating the back board about an axis along the second direction and positioning it at a predetermined angular position. Thus, by turning the rotary dial to rotate the back board, this makes it possible to switchably arrange the first and the second diffraction gratings, and to position them at the predetermined angular position.

A better understanding of the present invention will be further obtained by the following detailed description and accompanying drawings. These are shown only for illustration and should not be considered to limit the present invention.

BEST MODE FOR CARRYING OUT THE INVENTION

Hereinafter, referring to accompanying drawings, preferred embodiments of a spectroscopic system according to the present invention are described. Moreover, the same symbol is given to the same component throughout the drawings, and duplicated description will be omitted.

(First Embodiment)

Figure 1:
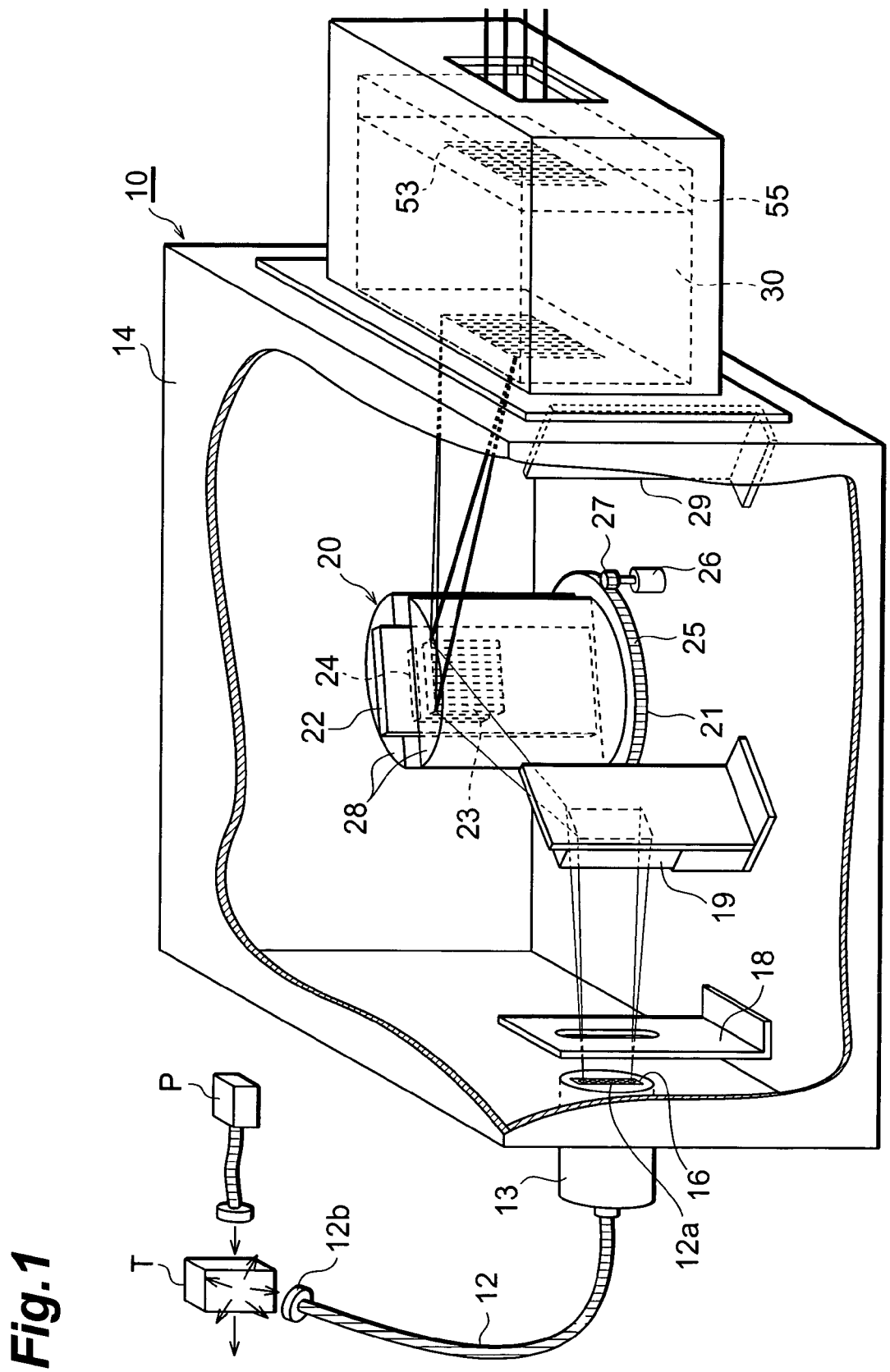
FIG. 1 is a perspective view showing a partial cutaway configuration of a spectroscopic system according to a first embodiment.
Figure 2A:
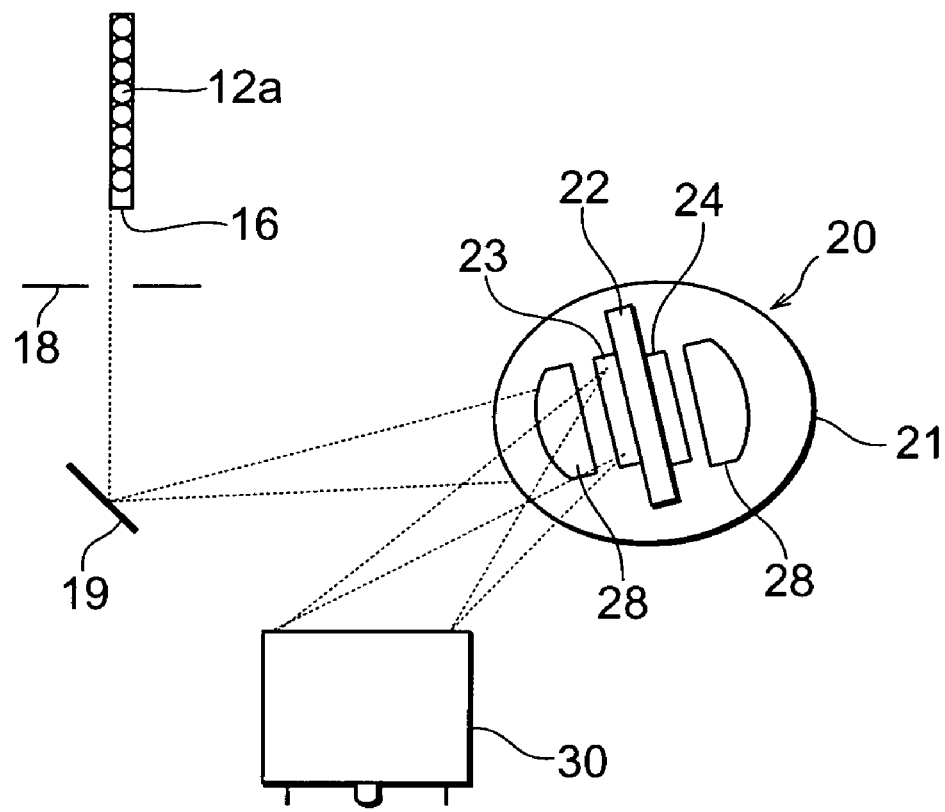
FIG. 2A is a view schematically showing a manner of a light transmission within the spectroscopic system according to the first embodiment.

FIG. 1 is a perspective view showing a partial cutaway configuration of a spectroscopic system according to a first embodiment, and FIG. 2A is a view schematically showing a manner of a light transmission within the spectroscopic system.

Figure 2B:
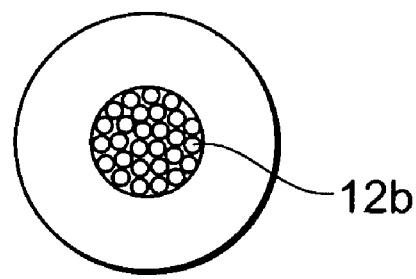
FIG. 2B is a view showing a configuration of an incident end of an optical fiber bundle.

As shown in FIG. 1, a spectroscopic system 10 comprises an optical fiber bundle 12 for receiving and guiding the light from a sample T at an incident end 12b. An emitting end 12a of this optical fiber bundle 12 is arranged in a vertical direction (first direction), as shown in FIG. 1 and FIG. 2A, and by a cylindrical emitting end section 13 including this emitting end 12a being fixed to a side face of a housing 14, the emitting end 12a faces a space in the housing 14. In addition, a long and narrow rectangular slit 16 is arranged so as to oppose the emitting end 12a of this optical fiber bundle 12. Moreover, as shown in FIG. 2B, the incident end 12b of the optical fiber bundle 12 is bundled into a circle shape, and is not arranged in one direction.

An aperture 18 is arranged on an optical path of the light which has passed through the slit 16. In addition, on an optical path of the light which has passed through the aperture 18, a plane mirror 19 for changing a traveling route of the light is arranged. In addition, on an optical path of the light whose traveling route has been changed by being reflected by the plane mirror 19, spectroscopic element arrangement means 20 is arranged.

As shown in FIG. 1 and FIG. 2A, the spectroscopic element arrangement means 20 is configured so that a first and a second diffraction gratings 23 and 24 may be respectively bonded on both principal planes of a back board 22 mounted on a disc-like base 21. The first and the second diffraction gratings 23 and 24 horizontally form a plurality of grooves which extend in the vertical direction (second direction) on a principal plane of a substrate, respectively, and it is designed that the number of grooves of the first diffraction grating 23 is fewer than the number of grooves of the second diffraction grating 24. For example, the first diffraction grating 23, in which the number of grooves is 600 per mm, can provide a spectrum in a wide wavelength band over 400 nm in wavelength band, meanwhile, the second diffraction grating 24, in which the number of grooves is 2400 per mm, can provide a spectrum in a narrow wavelength band over 100 nm in wavelength band. A gear 25 is formed on the side face of the disc-like base 21, and is engaged with a gear 27 of a motor 26. Thereby, the base 21 is rotated by rotatably driving the motor 26, and this makes it possible to switchably arrange the first diffraction grating 23 and the second diffraction grating 24 on the optical path. Moreover, on the base 21 and in front of the first and the second diffraction gratings 23 and 24, a semi-cylindrical-shaped lens 28 is located, respectively, and the light reflected by the plane mirror 19 is made to reliably enter into the diffraction grating.

Figure 3:
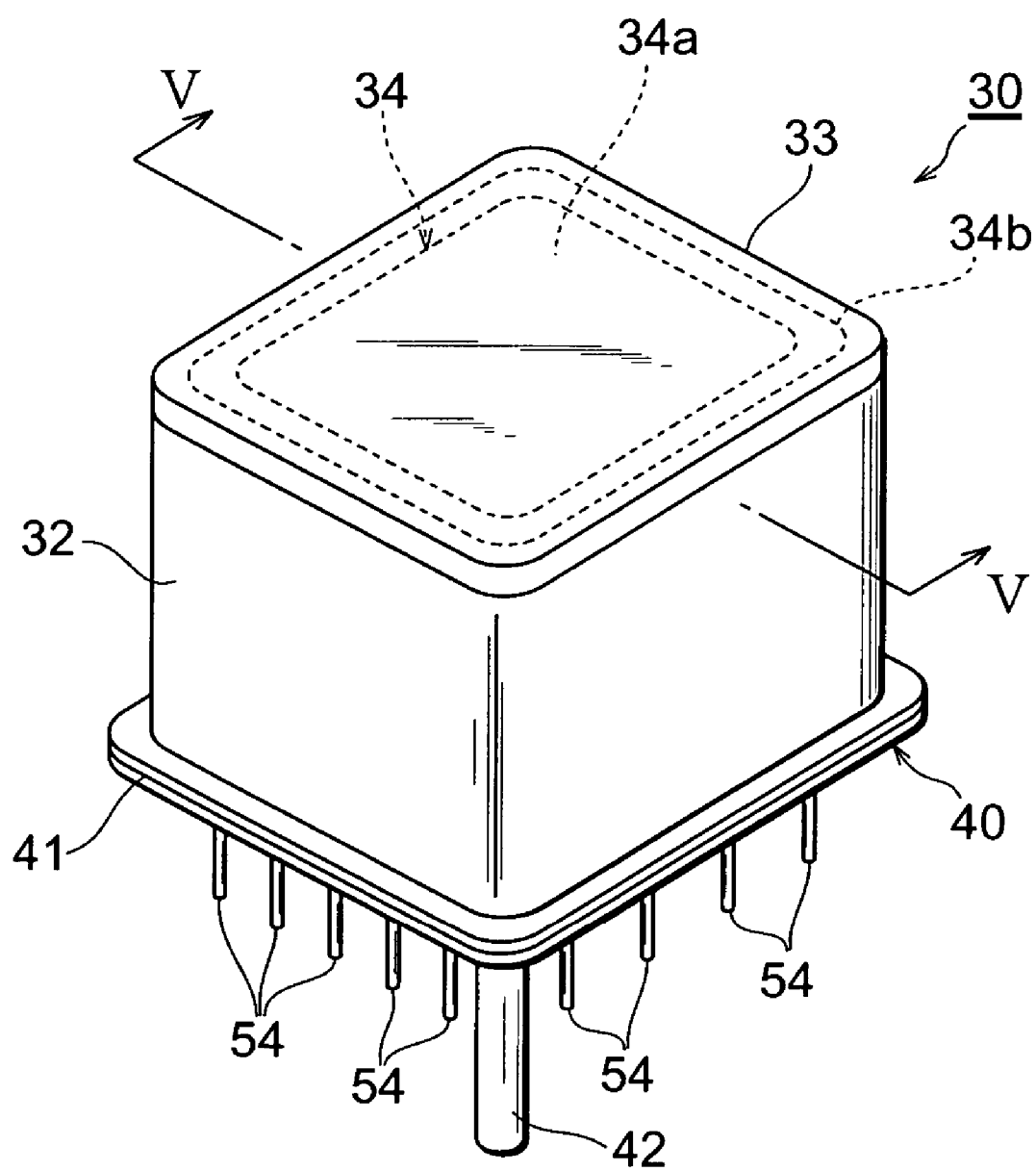
FIG. 3 is a perspective view showing a configuration of a photomultiplier tube.

On an optical path of the light which is demultiplexed by the diffraction grating of the spectroscopic element arrangement means 20, a photomultiplier tube 30 is arranged. As shown in FIG. 3, the photomultiplier tube 30 has a rectangular-tubelike-shaped metal housing 32, and a glass light-receiving surface plate 33 is hermetically mounted on one end section of this metal housing 32.

A photoelectric surface 34 for converting the light into electrons is arranged in an inner surface of this light-receiving surface plate 33. This photoelectric surface 34 can be formed by evaporating antimony on the light-receiving surface plate 33 and making an alkali metal react with antimony. The photoelectric surface 34 has an effective area 34a which is formed in the center of the light-receiving surface plate 33, and an outside region 34b is formed around the effective area 34a. Moreover, a film for cutting the second order light is preferably attached on this photoelectric surface 34.

Figure 4:
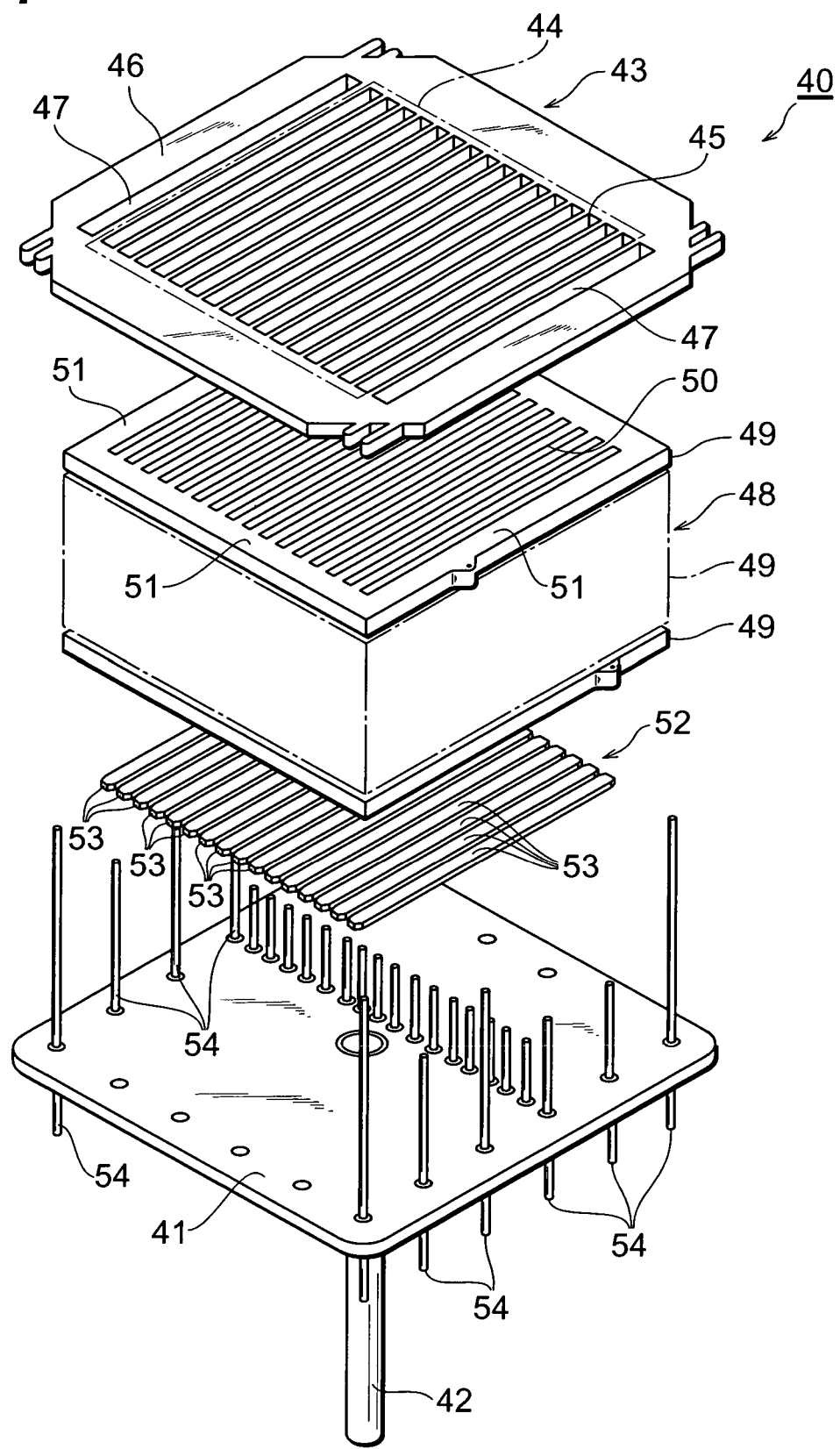
FIG. 4 is an exploded perspective view showing a configuration of an electron multiplier.

In addition, an opposite end section of the metal housing 32 is opened, and the electron multiplier 40 is inserted from this opened end section. As shown in FIG. 3 and FIG. 4, this electron multiplier 40 has a plate-shaped metal stem 41 which is hermetically mounted to the metal housing 32. A cylindrical metal exhaust pipe 42 for communicating an inside with an outside of the metal housing 32 is fixed in the center of this stem 41. After the metal housing 32 and the electron multiplier 40 are attached, this exhaust pipe 42 is not only used to exhaust air from the inside of the metal housing 32 with a vacuum pump or the like to make it into a vacuum state, but also used to enter the alkali metal steam, which is made to react to antimony evaporated on the photoelectric surface 34, into the metal housing 32.

As shown in FIG. 4, the electron multiplier 40 has a plate-shaped focusing electrode 43 arranged directly under the photoelectric surface 34, and as shown by the dot-dash line in FIG. 4, a focusing section 44 for focusing electrons which are entered from the effective area 34a of the photoelectric surface 34 is arranged at this focusing electrode 43. 16 slit-shaped channel openings 45 extending in the vertical direction are formed in this focusing section 44, and these openings 45 are arranged linearly and horizontally. In addition, a frame section 46 is arranged around the periphery of this focusing section 44, and slit-shaped dummy openings 47 are formed in this frame section 46. These dummy openings 47 are arranged in the same direction as the channel openings 45 of the focusing section 44, and one each of them is formed on both sides of the focusing section 44 in this arrangement direction.

In addition, the electron multiplier 40 has a block-shaped electron multiplier 48 which is arranged directly under the focusing electrode 43. This electron multiplier 48 is integrally formed by stacking eight plate-shaped dynodes 49, and 16 slit-shaped electron multiplier holes 50 for multiplying electrons at a position opposing the focusing section 44 of the focusing electrode 48 are formed in each dynode 49. In addition, an edge section 51 of a first stack of the dynode 49 faces against the frame section 46 of the focusing electrode 43 in the arrangement direction of the electron multiplier holes 50. Moreover, the 16 electron multiplier holes 50 are formed corresponding to the channel openings 45 of the focusing electrode 43, respectively.

Figure 5:
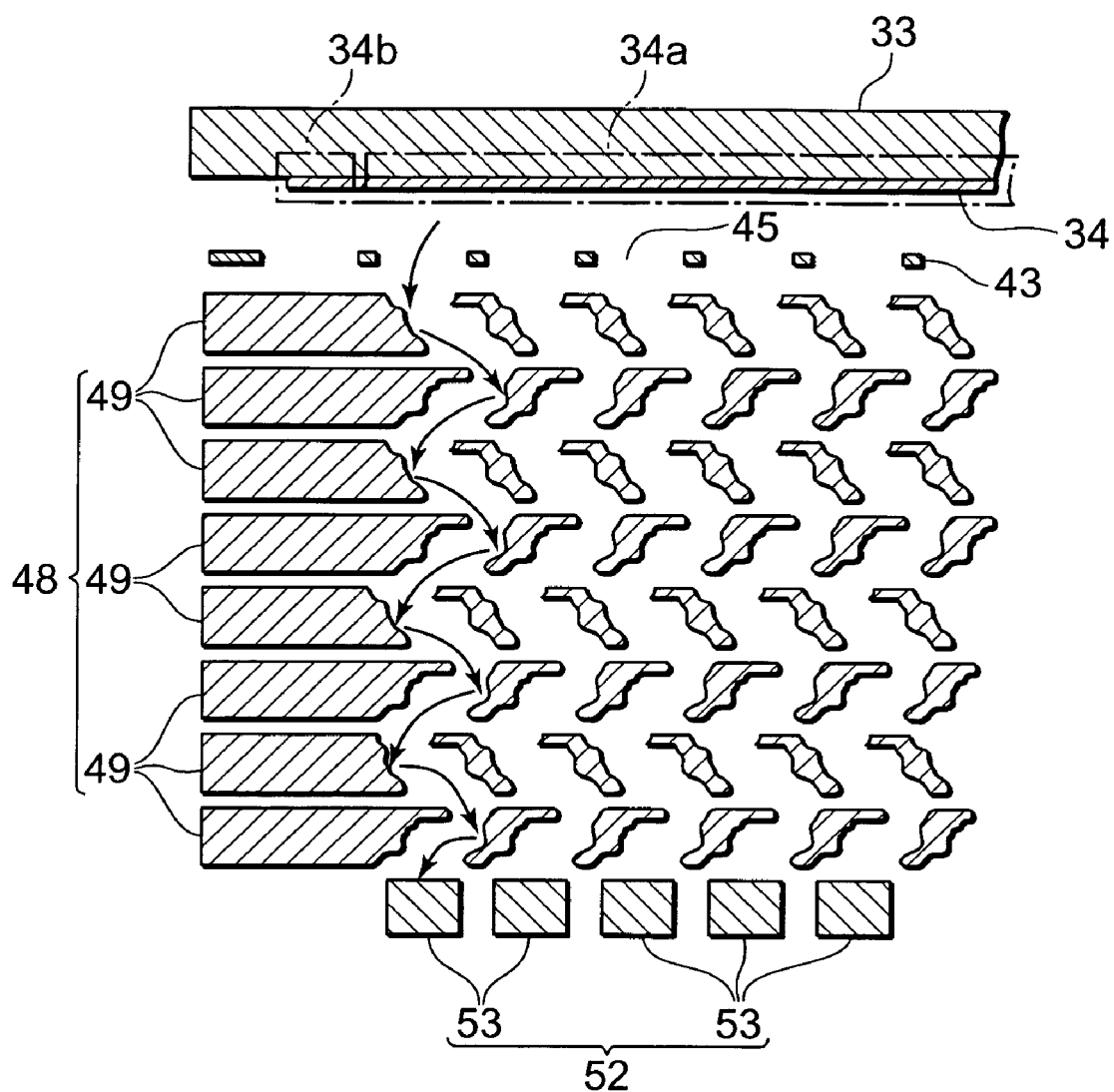
FIG. 5 is a sectional view along V—V line in FIG. 3.

Moreover, the electron multiplier 40 has an anode section 52 which is arranged under the electron multiplier 48. This anode section 52 consists of 16 independent long and narrow anodes 53 extending along the vertical direction (third direction). A direction where these anodes 53 extend is the same vertical direction as the arrangement direction of the emitting end 12a of the optical fiber bundle 12, and the forming direction of the groove of the first and the second diffraction gratings 23 and 24. As shown in FIG. 4 and FIG. 5, each anode 53 is arranged horizontally and linearly as well as the channel openings 45 and the electron multiplier holes 50, and corresponds to each electron multiplier hole 50 of the electron multiplier 48.

As shown in FIG. 4, the focusing electrode 43, the electron multiplier 48, and the anode section 52 are fixed by stem pins 54 which penetrate the stem 41 and extend perpendicularly from the outside of the metal housing 32. The stem pin 54 is connected with a bleeder 55 as shown in FIG. 1, and a predetermined electric potential is applied to the focusing electrode 43, the electron multiplier 48, and the anode section 52 by this pin 54. At this time, the photoelectric surface 34 and the focusing electrode 43 are set as the same electric potential, and the photoelectric surface 34, the electron multiplier 48, and the anode section 52 are set with electric potential higher in this order. Therefore, as the arrows of FIG. 5 show, photoelectrons generated in the photoelectric surface 34 pass through the focusing electrode 43 and the electron multiplier 48, and are detected by the anode section 52.

Moreover, as shown in FIG. 1, in a front face of the photomultiplier tube 30, a zero order light electric shielding baffle 29 is arranged, and the effect of the zero order light is reduced.

Next, a spectrum analysis method using the spectroscopic system 10 according to the first embodiment is described.

When performing a spectrum analysis in a wide wavelength band, as shown in FIG. 1, by driving the motor 26 first to rotate the base 21, the first diffraction grating 23 is arranged at a desired angular position on the optical path of the light reflected by the plane mirror 19. This angular position is beforehand set up so that the light, for example, in a wavelength band of 300 nm–700 nm, may be dispersed between both sides of the effective area 34a of the photoelectric surface 34 of the photomultiplier tube 30.

In this state, excitation light is irradiated towards the sample T from an excitation light source P, and the fluorescence emitted from the sample T is received at the incident end 12b of the optical fiber bundle 12. The light received at the incident end 12b is guided by the optical fiber bundle 12, and is emitted into the housing 14 from the emitting end 12a. Then, the light, which has passed through the rectangular slit 16 and been formed into the slit shape, is entered into the plane mirror 19 after stray light thereof has been removed by the aperture 18. The light, which is entered into the plane mirror 19, is reflected here, the optical path thereof is changed, and is entered into the first diffraction grating 23 of the spectroscopic element arrangement means 20 through the lens 28.

The light, which is entered into the first diffraction grating 23, is demultiplexed into individual wavelengths light, and the light in a wide wavelength range of 300 nm–700 nm is dispersed from the right edge to the left edge of the effective area 34a of the photoelectric surface 34 of the photomultiplier tube 30 and received. Thus, when detecting the light in the wide wavelength band, although a wavelength resolution is inferior to be about 25 nm, it can spectroscopically detect light in the wide wavelength range at a time, and good operation efficiency is achieved.

Next, when an analysis in a high wavelength resolution is required, the second diffraction grating 24 is arranged at a desired angular position on the optical path of the light reflected by the plane mirror 19 by driving the motor 26 to rotate the base 21. This angular position is beforehand set up so that the light, for example, in a wavelength band of 300 nm–400 nm, may be dispersed between both sides of the effective area 34a of the photoelectric surface 34 of the photomultiplier tube 30.

In this state, excitation light is irradiated towards the sample T from an excitation light source P, and the fluorescence emitted from the sample T is received at the incident end 12b of the optical fiber bundle 12. The light received at the incident end 12b is guided by the optical fiber bundle 12, and is emitted into the housing 14 from the emitting end 12a. Then, the light, which has passed through the rectangular slit 16 and been made into a slit shape, is entered into the plane mirror 19 after stray light thereof has been removed by the aperture 18. The light, which is entered into the plane mirror 19, is reflected here, the optical path of which is changed, and is entered into the second diffraction grating 24 of the spectroscopic element arrangement means 20 through the lens 28. The light which is entered into the second diffraction grating 24 is demultiplexed into individual wavelengths light, and the light in the narrow wavelength range of 300 nm–400 nm is dispersed from the right edge to the left edge of the effective area 34a of the photoelectric surface 32 of the photomultiplier tube 30 and received. Thus, when detecting the light in the narrow wavelength band, the wavelength resolution becomes about 6.3 nm, resulting in improvement in the wavelength resolution.

Here, in the spectroscopic system 10 according to this embodiment, since the angular position of the second diffraction grating 24 can be arbitrarily changed by rotating the base 21, the wavelength range of the light dispersed between both sides of the effective area 34a of the photoelectric surface 34 of the photomultiplier tube 30 can be selected in a range for every approximate 100 nm, such as 400 nm–500 nm, 500–600 nm. Thereby, this makes it possible to spectroscopically detect weak light with high sensitivity with high wavelength resolution over the wide wavelength band.

As mentioned above, the spectroscopic system 10 according to the first embodiment comprises the two-dimensional photomultiplier tube 30, which arranges the plurality of anodes 53 in parallel extending in the vertical direction, as a detector, and moreover, the plurality of anodes 53 of the photomultiplier tube 30 are arranged in the horizontal direction which intersects at a right angle to the vertical direction which is the arrangement direction of the emitting end 12a of the optical fiber bundle 12, and the forming direction of the groove of the first and the second diffraction gratings 23 and 24. Therefore, it is possible to detect light, which is emitted from the emitting end 12a of the optical fiber bundle 12 to pass through the slit 16 and is entered into the diffraction gratings 23 and 24 to be demultiplexed into individual wavelengths light, by each of the plurality of anodes 53 by sufficiently utilizing the effective area 34a of the photoelectric surface 34 of the photomultiplier tube 30. Thus, by sufficiently utilizing the effective area 34a of the photomultiplier tube 30, this makes it possible to spectroscopically detect weak light with higher sensitivity. In addition, since the spectroscopic element arrangement means 20 can switchably arrange the first diffraction grating 23 and the second diffraction grating 24, which have different groove densities, respectively, not only can a wider wavelength range be spectroscopically detected with high efficiency at a time by the first diffraction grating 23, but also a narrower wavelength range can be spectroscopically detected with high wavelength resolution by the second diffraction grating 24.

(Second Embodiment)

Next, a second embodiment of a spectroscopic system according to the present invention is described. Moreover, the same symbol is given to the same component as that of the first embodiment, and duplicated description will be omitted.

Figure 6:
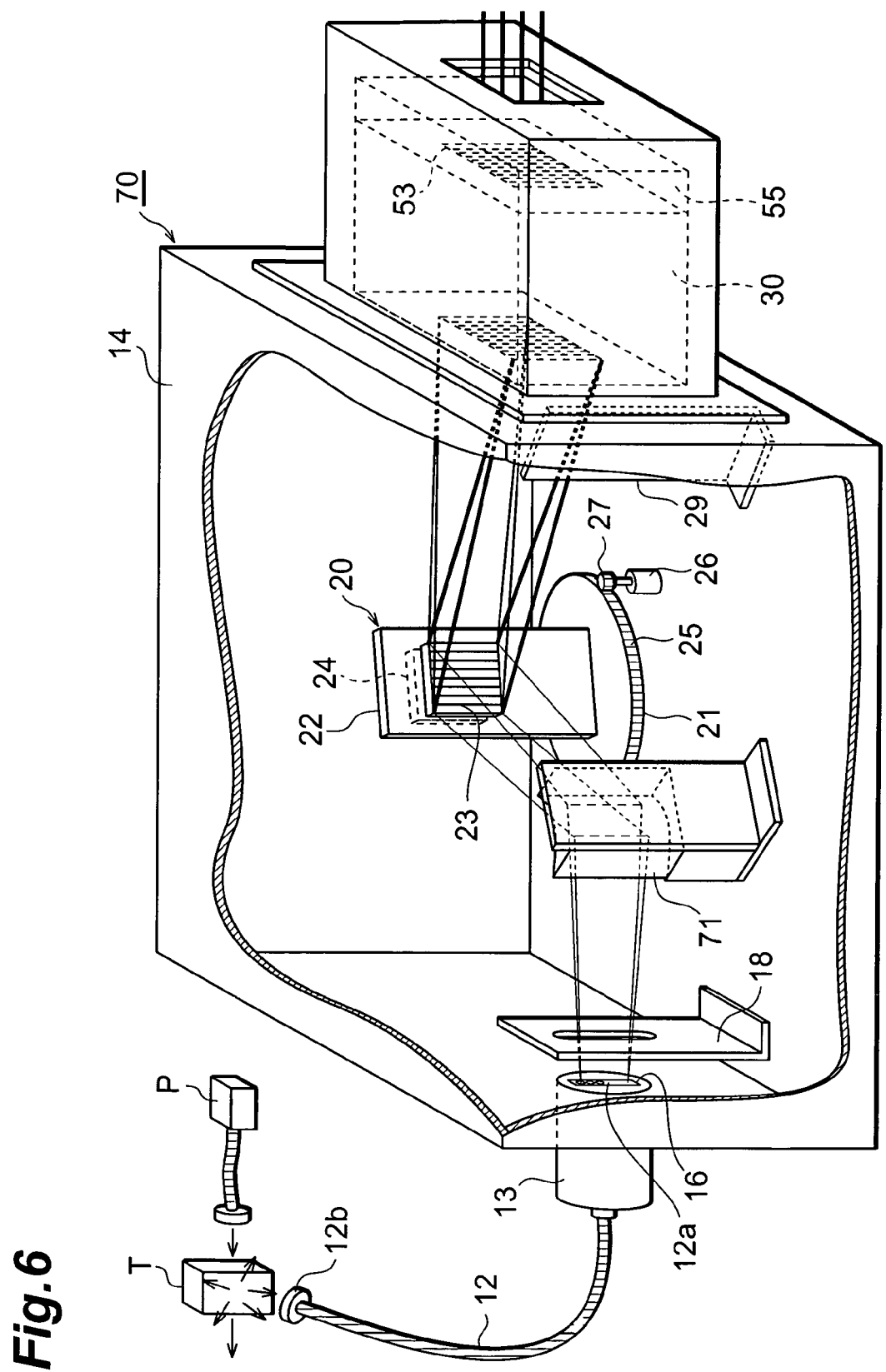
FIG. 6 is a perspective view showing a partial cutaway configuration of a spectroscopic system according to a second embodiment.

As shown in FIG. 6, the spectroscopic system according to the second embodiment 70 is a so-called Monk-Gillieson type spectroscopic system. As compared with the spectroscopic system 10 according to the first embodiment, this spectroscopic system 70 comprises a concave mirror 71 instead of the plane mirror 19. Then, since it thus comprises the concave mirror 71, the semi-cylindrical-shaped lens 28 is not arranged in front of the first and the second diffraction gratings 23 and 24.

The spectroscopic system 70 according to the second embodiment comprises the two-dimensional photomultiplier tube 30, which arranges the plurality of anodes 53 in parallel extending in the vertical direction, as a detector, and moreover, the plurality of anodes 53 of the photomultiplier tube 30 are arranged in the horizontal direction which intersects at a right angle to the vertical direction which is the arrangement direction of the emitting end 12a of the optical fiber bundle 12, and the forming direction of the groove of the first and the second diffraction gratings 23 and 24. Therefore, it is possible to detect light, which is emitted from the emitting end 12a of the optical fiber bundle 12 to pass through the slit 16 and is entered into the diffraction gratings 23 and 24 to be demultiplexed into individual wavelengths light, by each of the plurality of anodes 53 by sufficiently utilizing the effective area 34a of the photomultiplier tube 30. Thus, by sufficiently utilizing the effective area 34a of the photomultiplier tube 30, this makes it possible to spectroscopically detect weak light with higher sensitivity. In addition, since the spectroscopic element arrangement means 20 can switchably arrange the first diffraction grating 23 and the second diffraction grating 24, which have different groove densities, respectively, not only can a wider wavelength range be spectroscopically detected with high efficiency at a time by the first diffraction grating 23, but also a narrower wavelength range can be spectroscopically detected with high wavelength resolution by the second diffraction grating 24.

(Third Embodiment)

Next, a third embodiment of a spectroscopic system according to the present invention is described. Moreover, the same symbol is given to the same component as that of the first embodiment, and duplicated description will be omitted.

Figure 7:
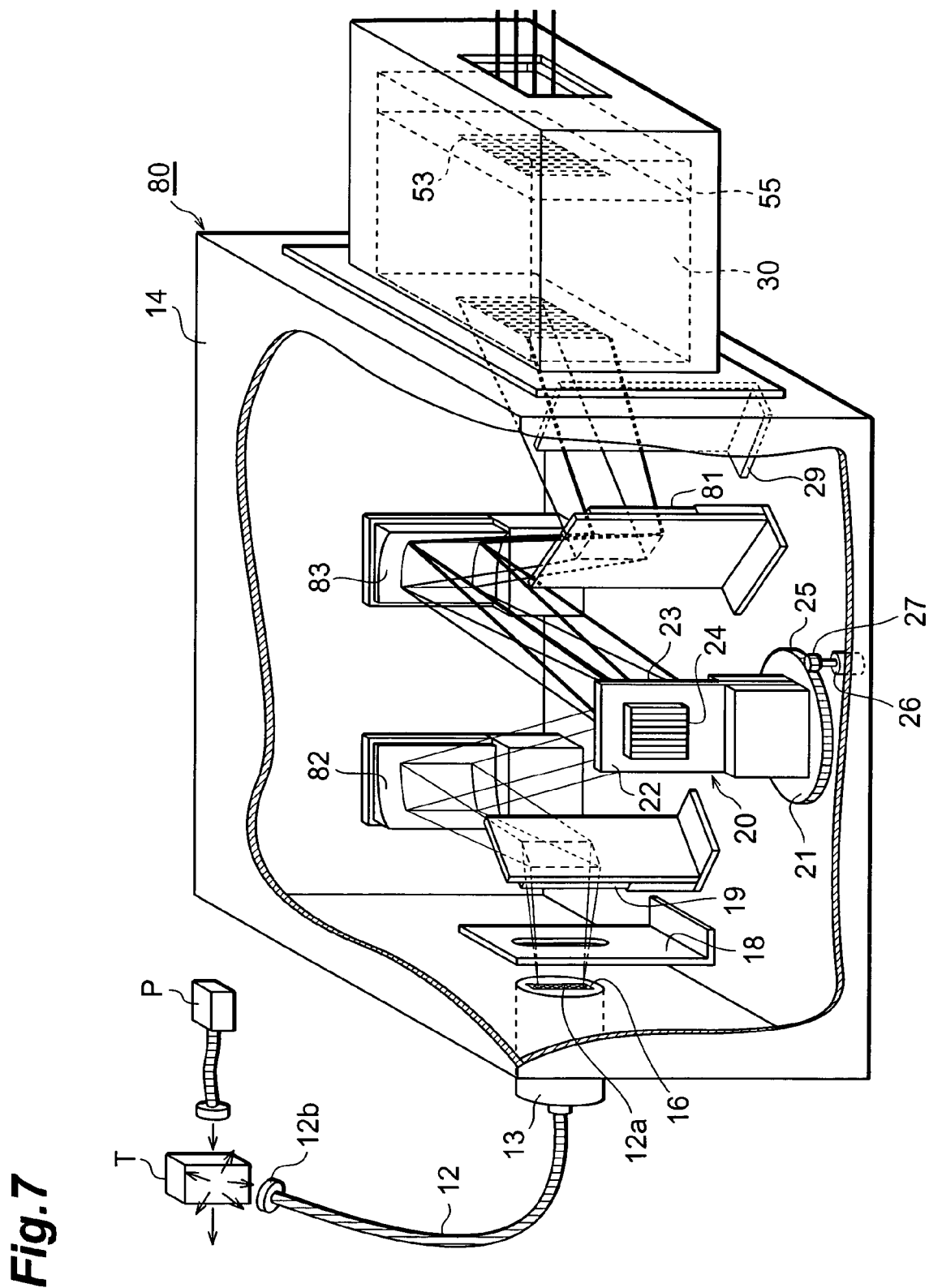
FIG. 7 is a perspective view showing a partial cutaway configuration of a spectroscopic system according to a third embodiment.

As shown in FIG. 7, the spectroscopic system according to the third embodiment 80 is a so-called Ebert type spectroscopic system. As compared with the spectroscopic system 10 according to the first embodiment, this spectroscopic system 80 comprises a new plane mirror 81 just in front of the photomultiplier tube 30. Then, it comprises concave mirrors 82 and 83 on an optical path from the plane mirror 19 to the spectroscopic element switching means 20, and on an optical path from the spectroscopic element switching means 20 to the plane mirror 81.

The spectroscopic system 80 according to the third embodiment also comprises the two-dimensional photomultiplier tube 30, which arranges the plurality of anodes 53 in parallel extending in the vertical direction, as a detector, and moreover, the plurality of anodes 53 of the photomultiplier tube 30 are arranged in the horizontal direction which intersects at a right angle to the vertical direction which is the arrangement direction of the emitting end 12a of the optical fiber bundle 12, and the forming direction of the groove of the first and the second diffraction gratings 23 and 24. Therefore, it is possible to detect light, which is emitted from the emitting end 12a of the optical fiber bundle 12 to pass through the slit 16 and is entered into the diffraction gratings 23 and 24 to be demultiplexed into individual wavelengths light, by each of the plurality of anodes 53 by sufficiently utilizing the effective area 34a of the photomultiplier tube 30. Thus, by sufficiently utilizing the effective area 34a of the photomultiplier tube 30, this makes it possible to spectroscopically detect weak light with higher sensitivity. In addition, since the spectroscopic element arrangement means 20 can switchably arrange the first diffraction grating 23 and the second diffraction grating 24, which have different groove densities, respectively, not only can a wider wavelength range can be spectroscopically detected with high efficiency at a time by the first diffraction grating 23, but also a narrower wavelength range be spectroscopically detected with high wavelength resolution by the second diffraction grating 24.

(Fourth Embodiment)

Next, a fourth embodiment of a spectroscopic system according to the present invention is described. Moreover, the same symbol is given to the same component as that of the first embodiment, and duplicated description will be omitted.

Although the basic configuration of the spectroscopic system 90 according to this embodiment is the same as that of the spectroscopic system 10 according to the first embodiment, the configuration is different with respect to the following.

Figure 9A:
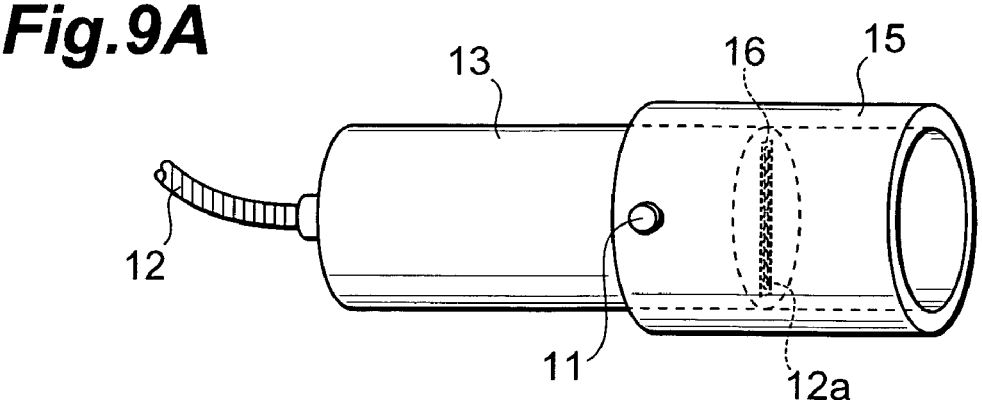
FIGS. 9A–C are views showing a manner of adjusting an optical path length by optical path length adjustment means in the spectroscopic system according to the fourth embodiment.
Figure 9B:
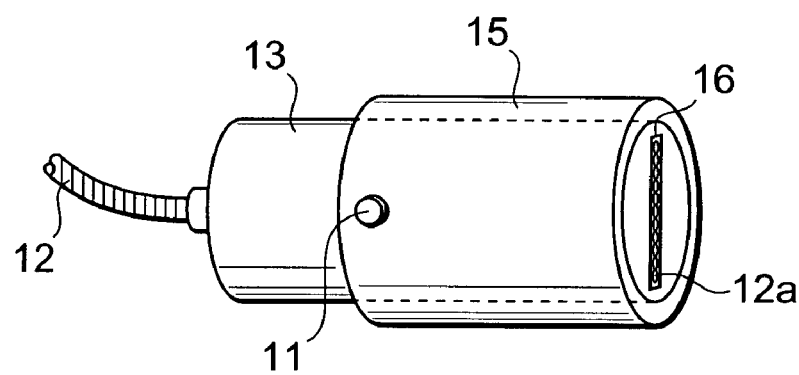
Figure 9C:
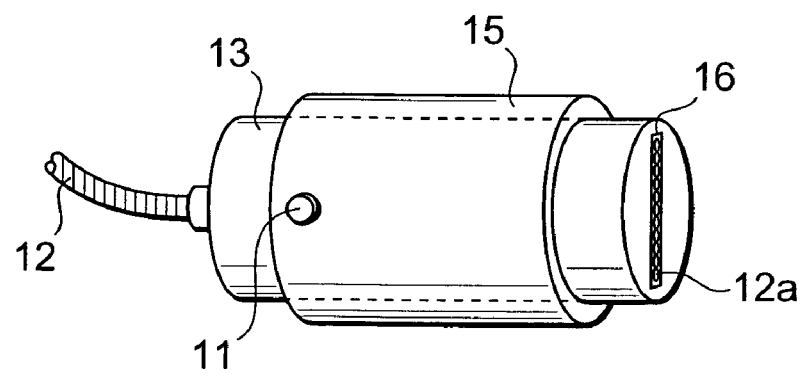

This spectroscopic system 90 has optical path length adjustment means of adjusting an optical path length of the light from the emitting end 12a of the optical fiber bundle 12 to the photomultiplier tube 30. That is, in the spectroscopic system 10 according to the first embodiment, the cylindrical emitting end section 13 including the emitting end 12a of the optical fiber bundle 12 has been fixed to the side face of the housing 14. In contrast to this, this spectroscopic system 90 comprises a cylindrical guide tube 15 for guiding the emitting end section 13. This guide tube 15 is fixed to the side face of the housing 14, and as shown in FIGS. 9A–9C, by sliding the emitting end section 13 within the guide tube 15, a position of the emitting end 12a is adjusted and the optical path length can be adjusted. As a result, this makes it possible to form a tight-focused image on the photomultiplier tube 30. Moreover, after being positioned at a predetermined position within the guide tube 15 for every measurement of different wavelength bands, the emitting end section 13 of the optical fiber bundle 12 is fixable by a screw 11, a ball plunger or the like.

Figure 8:
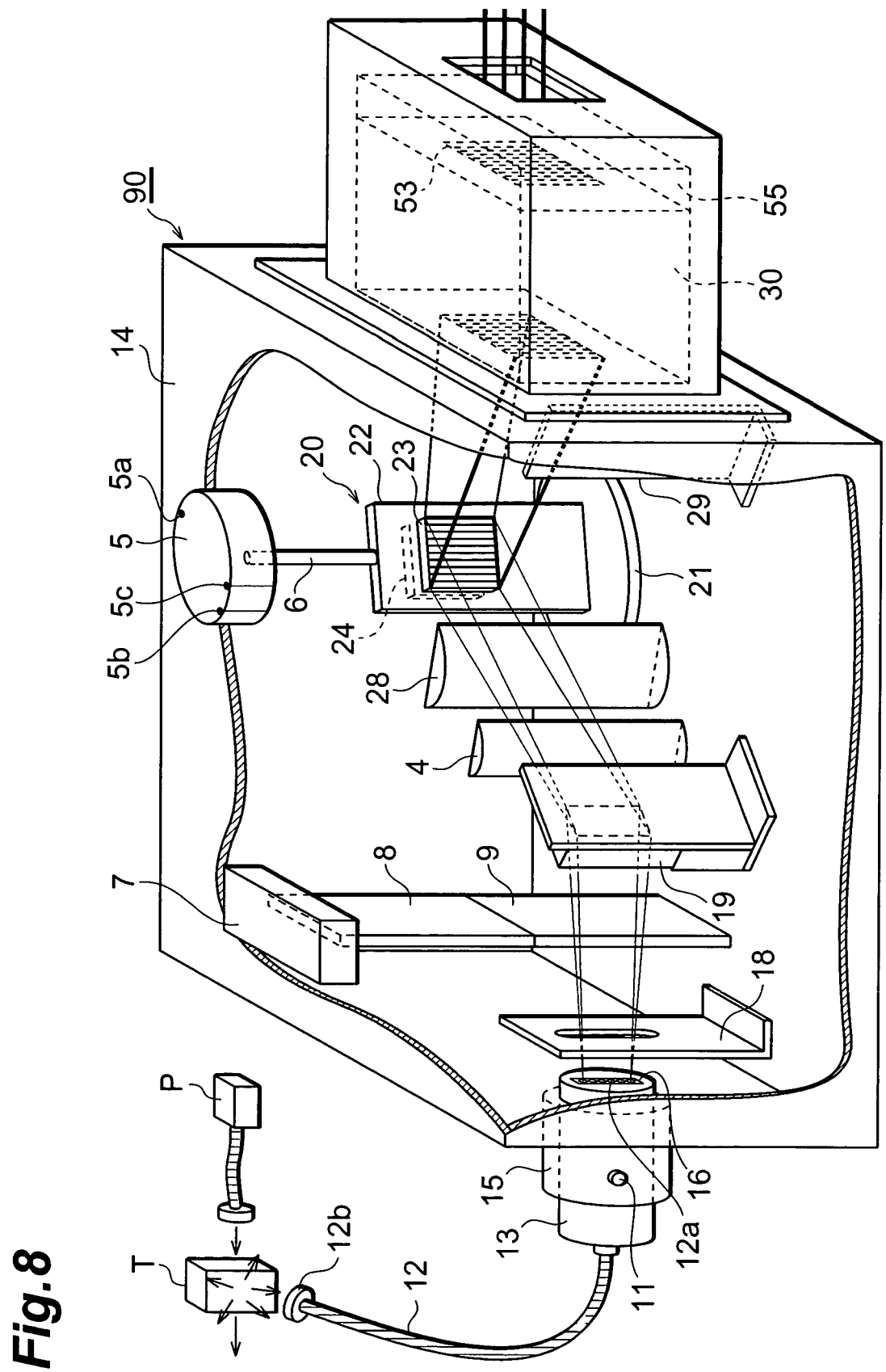
FIG. 8 is a perspective view showing a partial cutaway configuration of a spectroscopic system according to a fourth embodiment.
Figure 10:
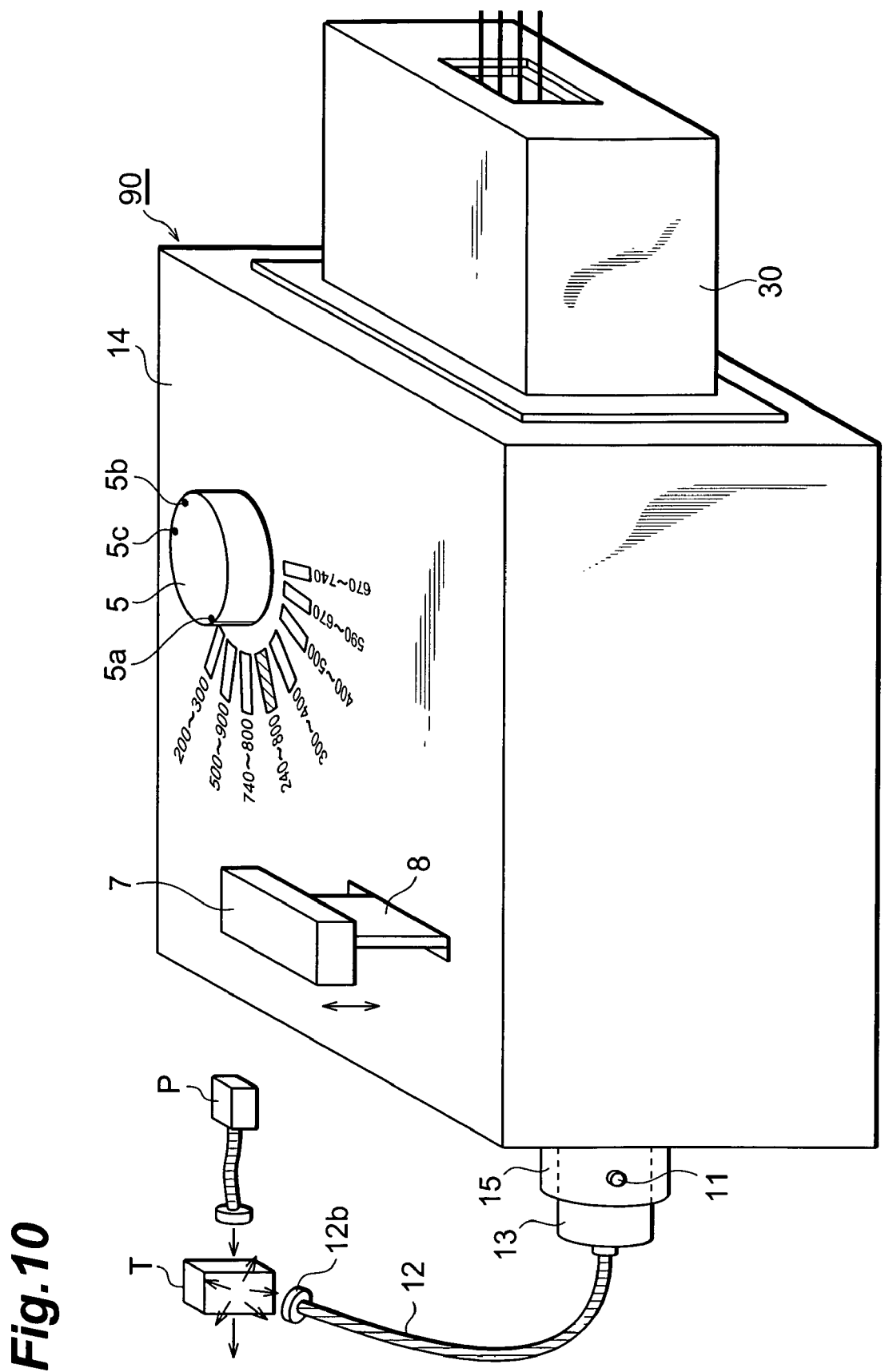
FIG. 10 is a perspective view showing an external appearance configuration of the spectroscopic system according to the fourth embodiment.

In addition, in this spectroscopic system 90, as shown in FIG. 8 and FIG. 10, a filter 9 for cutting the higher order light (second order light) is arranged on an optical path from the aperture 18 to the mirror 19. This filter 9 enables it to reduce the effect of the higher order light (second order light) at the time of measurement of the long wavelength band. This filter 9 is connected with a knob 7, which is arranged outside the housing 14, via a bearing clip 8. Therefore, as shown in FIG. 10, the filter 9 can be removed from the optical path by means of holding up the knob 7. Moreover, the filters 9 used for, for example, wavelength bands of 400 nm–670 nm and 670 nm or more are preferably prepared.

In the spectroscopic element arrangement means 20, the numbers of grooves of the first and the second diffraction gratings 23 and 24 are different from those of the spectroscopic system 10 according to the first embodiment. That is, the first diffraction grating 23, in which the number of grooves is 300 per mm, can provide a spectrum in a wide wavelength band over 240 nm–800 nm in wavelength band. Meanwhile, the second diffraction grating 24, in which the number of grooves is 1600 per mm, can provide a spectrum in a narrow wavelength band of 200 nm–800 nm in total in wavelength band. As shown in FIG. 8 and FIG. 10, the back board 22 extending along the vertical direction is connected with the disc-like rotary dial 5, which is arranged outside the housing 14, via a coupling rod 6. The back board 22 is rotated by rotating this rotary dial 5 manually, an angular position of the back board 22 to an axis along the vertical direction is set up, and the first diffraction grating 23 and the second diffraction grating 24 can be switchably arranged at a predetermined angular position on the optical path.

In addition, in the spectroscopic system 90 according to this embodiment, one semi-cylindrical-shaped lens 28 is arranged on an optical path from the plane mirror 19 to the first and the second diffraction gratings 23 and 24, and outside the base 21. According to this lens 28, the light reflected by the plane mirror 19 is reliably entered into the diffraction gratings 23 and 24. Moreover, since there is no need for the lens 28 to be arranged on the base 21 and in front of the first and the second diffraction gratings 23 and 24, respectively, like the spectroscopic system 10 according to the first embodiment, assembly steps and manufacturing costs can be reduced due to the reduction in the number of lenses 28.

Furthermore, in the spectroscopic system 90 according to this embodiment, on an optical path from the plane mirror 19 to the lens 28, the cylindrical lens 4 for removing a chromatic aberration, a spherical aberration or the like due to the lens 28 is arranged.

Next, a spectrum analysis method using the spectroscopic system 90 according to the fourth embodiment is described.

Figure 11A:
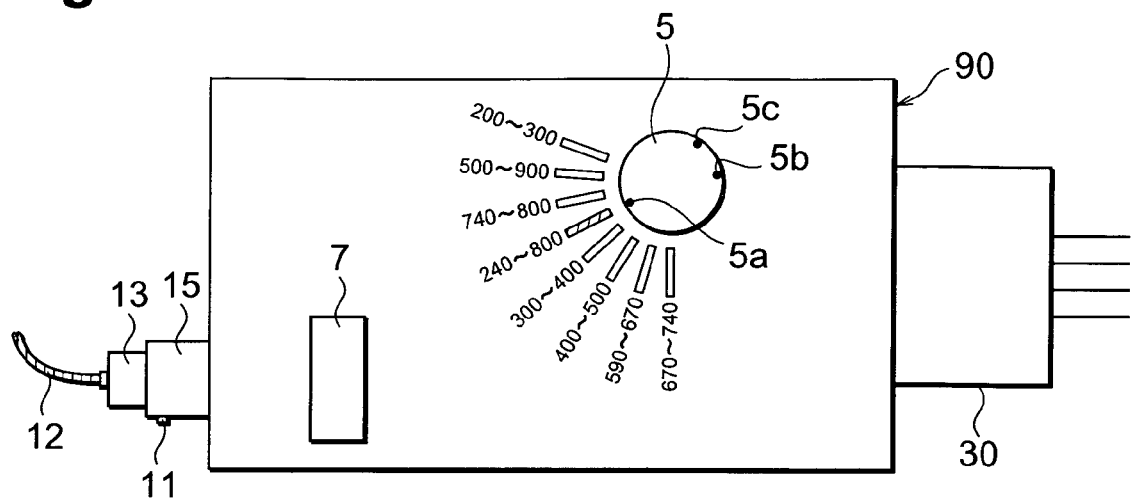
FIG. 11A, FIG. 12A, and FIG. 13A are views showing a manner of switching an arrangement of a diffraction grating by turning a rotary dial in the spectroscopic system according to the fourth embodiment.
Figure 11B:
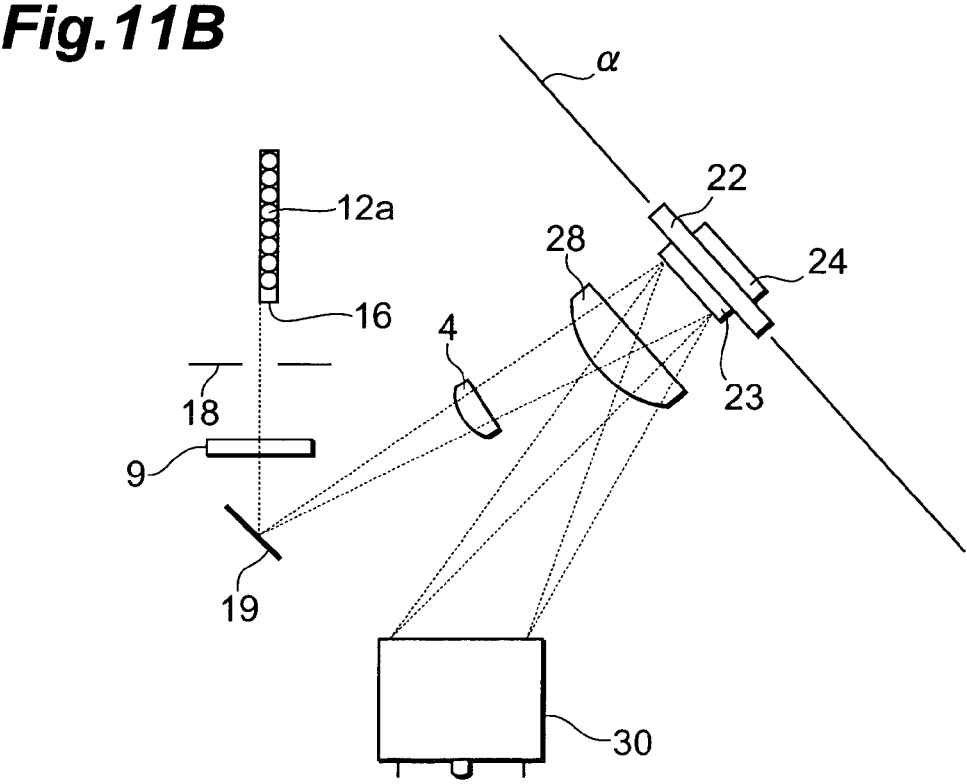
FIG. 11B, FIG. 12B, and FIG. 13B are views showing a manner of arrangement of the diffraction grating in each case of FIG. 11A, FIG. 12A, and FIG. 13A.

When performing a spectrum analysis in a wide wavelength band, as shown in FIG. 11A, by rotating the rotary dial 5 first, indication 5a is set at a scale of 240 nm–800 nm drawn on the housing 14. Thereby, as shown in FIG. 11B, on the optical path of the light reflected by the plane mirror 19, the first diffraction grating 23 is arranged at a desired angular position. Moreover, this angular position is beforehand set up so that the light with a wavelength band of 240 nm–800 nm may be dispersed between both sides of the effective area 34a of the photoelectric surface 34 of the photomultiplier tube 30.

Figure 12A:
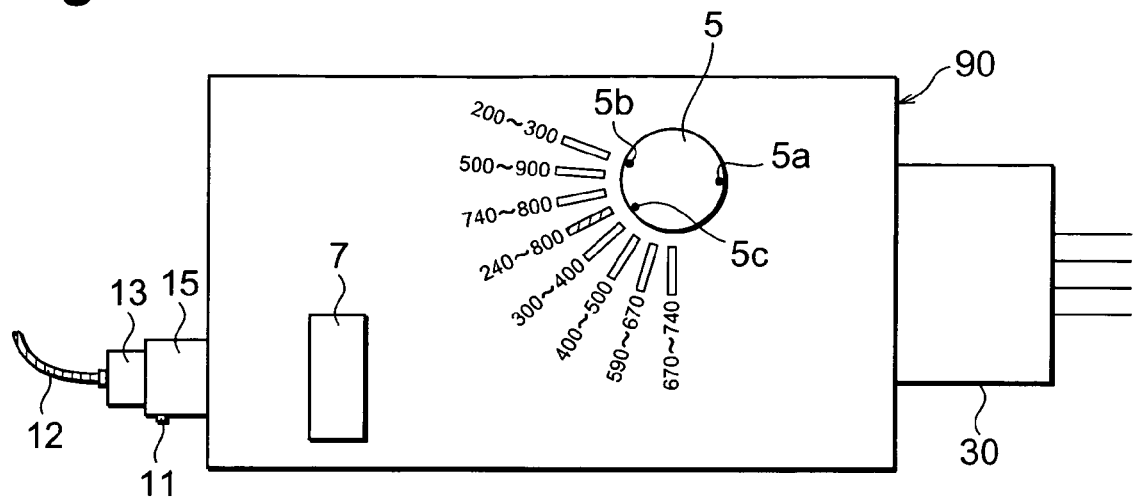
Figure 12B:
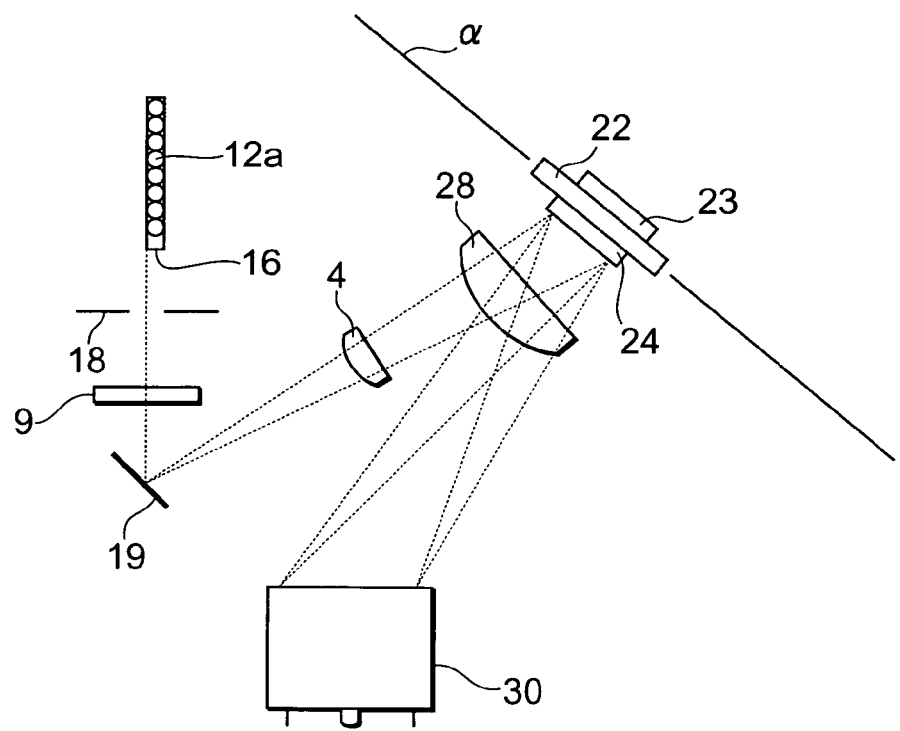

Next, when an analysis in a high wavelength resolution is required, by rotating the rotary dial 5, either of indication 5b or 5c is set at a scale drawn on the housing 14. For example, at the time of measurement in a wavelength band of 200 nm–300 nm, as shown in FIG. 12A, indication 5b is set at a scale of 200 nm–300 nm drawn on the housing 14. Thereby, as shown in FIG. 12B, on the optical path of the light reflected by the plane mirror 19, the second diffraction grating 24 is arranged at a desired angular position. Moreover, this angular position is beforehand set up so that the light with the wavelength band of 200 nm–300 nm may be dispersed between both sides of the effective area 34a of the photoelectric surface 34 of the photomultiplier tube 30.

Figure 13A:
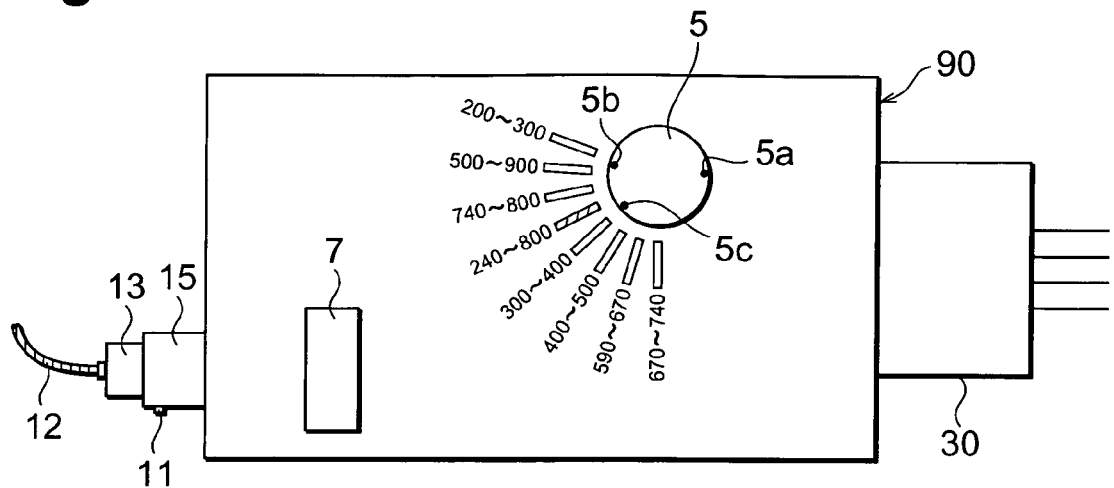
Figure 13B:
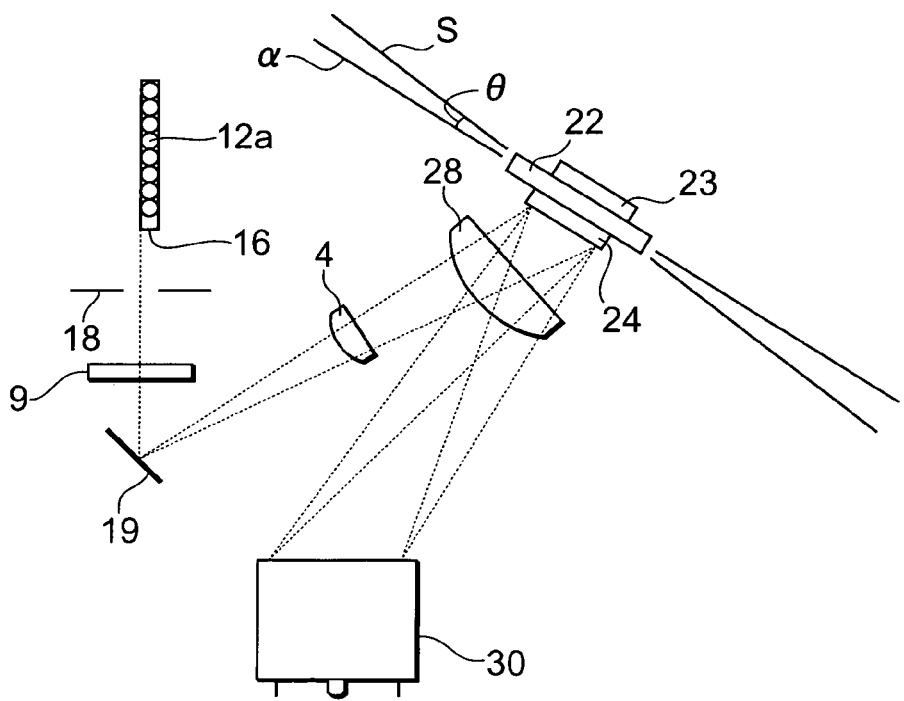

Furthermore, at the time of measurement in the wavelength band of 300 nm–400 nm, as shown in FIG. 13A, indication 5c is set at a scale of 300 nm–400 nm drawn on the housing 14. Thereby, as shown in FIG. 13B, the second diffraction grating 24 is arranged at a desired angular position on the optical path of the light reflected by the plane mirror 19. Moreover, this angular position is beforehand set up so that the light with the wavelength band of 300 nm–400 nm may be dispersed between both sides of the effective area 34a of the photoelectric surface 34 of the photomultiplier tube 30. With reference to an inclination S of the back board 22 at the time of measurement in the wavelength band of 200 nm–300 nm, this angular position is a position α where the back board 22 is tilted by a predetermined angle θ.

Moreover, at the time of measurement in a wavelength band of 400 nm–500 nm, indication 5c is set at a scale of 400 nm–500 nm drawn on the housing 14. In addition, at the time of measurement in a wavelength band of 500 nm–590 nm, indication 5b is set at a scale of 500 nm–590 nm drawn on the housing 14. In addition, at the time of measurement in a wavelength band of 590 nm–670 nm, indication 5c is set at a scale of 590 nm–670 nm drawn on the housing 14. In addition, at the time of measurement in a wavelength band of 670 nm–740 nm, indication 5c is set at a scale of 670 nm–740 nm drawn on the housing 14. Furthermore, at the time of measurement in a wavelength band of 740 nm–800 nm, indication 5b is set at a scale of 740 nm–800 nm drawn on the housing 14. Moreover, at the time of measurement in a long wavelength band, the filter 9 for cutting the high order (second order) light is preferably inserted in the optical path.

Thus, by sequentially setting either of indication 5b or 5c of the rotary dial 5 at the scale drawn on the housing 14, the angle θ described above becomes large sequentially, and the light in each wavelength band is dispersed between both sides of the effective area 34a of the photoelectric surface 34 of the photomultiplier tube 30.

Moreover, a plurality of scales of the narrow wavelength band on the housing 14 are arranged on both sides of the scale of 240 nm–800 nm which is the wide wavelength band, and at the time of measurement in the narrow wavelength band, either of two indications 5b and 5c of the rotary dial 5 has been set at the scale. Thus, by configuring so that either of two indications 5b and 5c may be set at the scale of the narrow wavelength band arranged discontinuously, this makes it possible to adjust the angular position of the second diffraction grating 24 finely.

The spectroscopic system 90 according to the fourth embodiment comprises the two-dimensional photomultiplier tube 30, which arranges the plurality of anodes 53 in parallel extending in the vertical direction, as a detector, and moreover, the plurality of anodes 53 of the photomultiplier tube 30 are arranged in the horizontal direction which intersects at a right angle to the vertical direction which is the arrangement direction of the emitting end 12a of the optical fiber bundle 12, and the forming direction of the groove of the first and the second diffraction gratings 23 and 24. Therefore, it is possible to detect light, which is emitted from the emitting end 12a of the optical fiber bundle 12 to pass through the slit 16 and is entered into the diffraction gratings 23 and 24 to be demultiplexed into individual wavelengths light, by each of the plurality of anodes 53 by sufficiently utilizing the effective area 34a of the photomultiplier tube 30. Thus, by sufficiently utilizing the effective area 34a of the photomultiplier tube 30, this makes it possible to spectroscopically detect weak light with higher sensitivity. In addition, since the spectroscopic element arrangement means 20 can switchably arrange the first diffraction grating 23 and the second diffraction grating 24, which have different groove densities, respectively, not only can a wider wavelength range be spectroscopically detected with high efficiency at a time by the first diffraction grating 23, but also a narrower wavelength range can be spectroscopically detected with high wavelength resolution by the second diffraction grating 24.

Moreover, the spectroscopic system according to the present invention is not limited to the embodiment described above and various modifications can be made.

For example, in the embodiment described above, although the configuration where the first diffraction grating 23 and the second diffraction grating 24 are switchably arranged by rotating the disc-like base 21 has been described, without being limited to this, it may be configured so that the first diffraction grating 23 and the second diffraction grating 24 may be switchably arranged by means of horizontal sliding movement.

In addition, the spectroscopic systems according to the first to the third embodiment 10, 70, and 80 may also comprise the optical path length adjustment means explained in the spectroscopic system 90 according to the fourth embodiment.

In addition, in the embodiment described above, although the two-dimensional linear PMT, in which the number of the anodes 53 is 16, has been described as the photomultiplier tube 30, a two-dimensional linear PMT, in which the number of the anodes 53 is 32, may be used.

Based on the above description, it is apparent that the present invention may be modified variously. Such modifications should not be recognized as departing from the sprit and the scope of the present invention, and improvements which are apparent for all skilled in the art are included in the scope of the appended Claims.

INDUSTRIAL APPLICABILITY

According to the present invention, a spectroscopic system, which can spectroscopically detect weak light with higher sensitivity with high wavelength resolution, is provided.

The invention claimed is:

1. A spectroscopic system, comprising:
   an optical fiber bundle whose emitting end is arranged in a first direction;
   a slit which is arranged so as to oppose said emitting end of said optical fiber bundle;
   spectroscopic element arrangement means which can switchably arrange either a first diffraction grating in which grooves extending along a second direction are arranged at a predetermined groove density in a direction to intersect said second direction or a second diffraction grating in which grooves extending along said second direction are arranged at a groove density larger than that of said first diffraction grating in the direction to intersect said second direction, on an optical path of light which is emitted from said emitting end of said optical fiber bundle and passes through said slit; and
   a photomultiplier tube, in which a plurality of anodes extending along a third direction, are arranged in a direction to intersect said third direction;
   wherein said first direction, said second direction, and said third direction are substantially the same direction.

2. A spectroscopic system according to claim 1, comprising optical path length adjustment means of adjusting an optical path length of the light from said emitting end of said optical fiber bundle to said photomultiplier tube.

3. A spectroscopic system according to claim 2, wherein said optical path length adjustment means has a guide tube for guiding said emitting end of said optical fiber bundle in a predetermined direction.

4. A spectroscopic system according to claim 1, comprising a filter for cutting higher order light, removably arranged on an optical path.

5. A spectroscopic system according to claim 1, comprising a first lens for guiding the light to said first diffraction grating or said second diffraction grating; and a cylindrical lens arranged in front of said first lens.

6. A spectroscopic system according to claim 1, wherein said spectroscopic element arrangement means has a back-board which mounts said first and said second diffraction gratings and extends in said second direction; and a rotary dial for rotating this back board about an axis along said second direction and positioning it at a predetermined angular position.

* * * * *